US012624335B2

(12) United States Patent
Zhang et al.

(10) Patent No.: US 12,624,335 B2
(45) Date of Patent: May 12, 2026

(54) PRODUCTION METHOD OF RECOMBINANT *Escherichia coli* AND HIGH-PURITY URSODEOXYCHOLIC ACID

(71) Applicants: Tian Zhang, Xi'an (CN); Tong Xue, Xi'an (CN); Lihui Zhu, Xi'an (CN)

(72) Inventors: Tian Zhang, Xi'an (CN); Tong Xue, Xi'an (CN); Lihui Zhu, Xi'an (CN)

(73) Assignee: XI'AN YUEDA BIOTECHNOLOGY CO., LTD., Xi'an (CN)

( * ) Notice: Subject to any disclaimer, the term of this patent is extended or adjusted under 35 U.S.C. 154(b) by 486 days.

(21) Appl. No.: 18/064,272

(22) Filed: Dec. 11, 2022

(65) Prior Publication Data

US 2023/0287333 A1    Sep. 14, 2023

(30) Foreign Application Priority Data

Mar. 11, 2022    (CN) .......................... 202210285129.6

(51) Int. Cl.
     *C12N 1/205*      (2026.01)
     *C12N 9/04*      (2006.01)
     (Continued)

(52) U.S. Cl.
     CPC .......... *C12N 1/205* (2021.05); *C12N 9/0006* (2013.01); *C12N 15/70* (2013.01);
     (Continued)

(58) Field of Classification Search
     CPC .......... C12N 1/205; C12N 15/70; C12N 1/20; C12N 2800/22; C12R 2001/19; C12Y 101/01047; C12Y 101/01201; C12P 33/02
     See application file for complete search history.

(56) References Cited

FOREIGN PATENT DOCUMENTS

CN      109402212 A   *   3/2019   .......... C12N 9/0006
CN      112852652 A      5/2021
     (Continued)

OTHER PUBLICATIONS

Ferrandi et al. (2012). "In search of sustainable chemical processes: cloning, recombinant expression, and functional characterization of the 7alpha- and 7beta-hydroxysteroid dehydrogenases from Clostridium absonum." Appl. Microbiol. Biotechnol., 95:1221-1233. (Year: 2012).*

(Continued)

*Primary Examiner* — Daniel E Kolker
*Assistant Examiner* — Bailey M Morgan

(57)      ABSTRACT

The present invention belongs to the field of bioengineering technologies, and in particular, to a production method of recombinant *Escherichia coli* (*E. coli*) and high-purity ursodeoxycholic acid (UDCA). The present invention constructs novel double-enzyme co-expression gene engineered bacteria, that is, recombinant *E. coli*. The bacteria simultaneously expresses 7β-hydroxysteroid dehydrogenase (7β-HSDH) and glucose dehydrogenase (GDH). The bacteria is applicable to the production of high-purity UDCA. The yield of a target product is increased through the joint expression and application of 7β-HSDH and GDH. The production method of high-purity UDCA in the present invention is simple, generates a small amount of impurities in a production process, is a green process that satisfies environmental protection requirements, and has significant industrial application value.

1 Claim, 2 Drawing Sheets

Specification includes a Sequence Listing.

(51) Int. Cl.
    *C12N 15/70*       (2006.01)
    *C12R 1/19*       (2006.01)

(52) U.S. Cl.
    CPC ... *C12R 2001/19* (2021.05); *C12Y 101/01047*
          (2013.01); *C12Y 101/01201* (2013.01)

(56) References Cited

FOREIGN PATENT DOCUMENTS

| | | | | |
|---|---|---|---|---|
| CN | 113913317 A | | 1/2022 | |
| CN | 114015712 A | | 2/2022 | |
| CN | 114592027 A | * | 6/2022 | ............. C12N 15/70 |
| JP | 2014502490 A | | 2/2014 | |
| JP | 2021509804 A | | 4/2021 | |

OTHER PUBLICATIONS

Lee et al. (2013). "Contribution of the 7beta-hydroxysteroid dehydrogenase from Rhuminococcus gnavus N53 to ursodeoxycholic acid formation in the human colon." J. Lipid Res., 54(11):3062-3069. (Year: 2013).*

Espacenet machine translation of CN114592027A description as obtained online at worldwide.espacenet.com [retrieved on Oct. 29, 2025]. Retrieved from the internet: https://worldwide.espacenet.com/patent/search/family/081816064/publication/CN114592027A?search_type=patents&q=cn114592027a. (Year: 2022).*

Xu et al. (2007). "High-level expression of recombinant glucose dehydrogenase and its application in NADPH regeneration." J Ind Microbiol Biotechnol, 34(1):83-90. (Year: 2007).*

Espacenet machine translation of CN109402212A description as obtained online at worldwide.espacenet.com [retrieved on May 19, 2025]. Retrieved from the internet: https://worldwide.espacenet.com/patent/search/family/065456367/publication/CN109402212A?q=cn109402212a. (Year: 2019).*

Ferrandi et al. (2012). "In search of sustainable chemical processes: cloning, recombinant expression, and functional characterization of the 7a- and 7B-hydroxysteroid dehydrogenases from Clostridium absonum." Appl. Microbiol. Biotechnol., 95: 1221-1233. (Year: 2012).*

Kole and Altosaar. (1985). "Conversion of chenodeoxycholic acid to ursodeoxycholic acid by Clostridium absonum in culture and by immobilized cells." FEMS Microbiology Letters, 28(1):69-72. (Year: 1985).*

Jing et al. (2010). "GenBank: AY930464.1 Bacillus megaterium strain AS1.223 glucose dehydrogenase gene, complete cds". As obtained online at ncbi.nlm.nih.gov [retrieved on Oct. 29, 2025]. Retrieved from the internet: ncbi.nlm.nih.gov/nucleotide/AY930464.1?report=genbank&log$=nuclalign&blast_ra (Year: 2010).*

Mingmin Zheng et al., "Engineering 7beta-hydroxysteroid dehydrogenase for enhanced ursodeoxycholic acid production by multi-objective directed evolution" J. Agric. Food Chem. 2017, 65, 6, 1178-1185 (Jan. 24, 2017).

Ming-Min Zheng et al., "Two-step enzymatic synthesis of ursodeoxycholic acid with a new 7beta-hydroxysteroid dehydrogenase from Ruminococcus torques" Process Biochemistry 50 (2015) 598-604 (Jan. 17, 215).

* cited by examiner

PRODUCTION METHOD OF RECOMBINANT *Escherichia coli* AND HIGH-PURITY URSODEOXYCHOLIC ACID This application claims priority to Chinese Patent Application No. CN 202210285129.6, filed on Mar. 11, 2022, which is incorporated by reference for all purposes as if fully set forth herein.

A Sequence Listing XML file named "10025_0099.xml" created on Feb. 22, 2026, and having a size of 5,215 bytes, is filed concurrently with the specification. The sequence listing contained in the XML file is part of the specification and is herein incorporated by reference in its entirety.

TECHNICAL FIELD

The present invention belongs to the field of bioengineering technologies, and in particular, to a production method of recombinant *Escherichia coli* (*E. coli*) and high-purity ursodeoxycholic acid (UDCA).

BACKGROUND

As a traditional Chinese medicine active ingredient, UDCA (3a,7β-dihydroxy-5β-cholan-24-oic acid) has found very wide clinical application and is of excellent pharmaceutical value. UDCA produces an excellent therapeutic effect in treating gallstones, facilitated liver transplantation, bile reflux gastritis, alcoholic liver, biliary cirrhosis, and drug-induced hepatitis, leading to high market demand.

At present, UDCA is mainly prepared from a natural source and through synthesis. The natural source is bear gallbladders or bile extracted from live bears that are protected by animal protection laws, and an extraction source is limited, causing a gradual decline in the source of natural bear gallbladders. In the synthesis, UDCA is chemically synthesized using chenodeoxycholic acid (CDCA) extracted from readily available cow or goose bile, and 7-OH undergoes a conformational change by using an oxidation-reduction method. However, there are a series of problems such as a complex reaction process, low selectivity, stringent reaction conditions, high energy consumption, and serious contamination. Especially, toxic and hazardous reagents are required during protection and deprotection, which severely limits the industrial application of chemical methods. At present, UDCA produced using chemical methods accounts for a market share of approximately 30% and has a relatively low purity of approximately 80%, which is far from satisfying the requirements for the usage and quality of UDCA in the market.

Compared with chemical epimerization, the biological synthesis of UDCA is efficient and relatively environmentally friendly. Microbial transformation or biological enzyme catalysis mainly involves the expansion of 7α-hydroxysteroid dehydrogenase (7α-HSDH) and 7β-hydroxysteroid dehydrogenase (7β-HSDH). *Clostridium limosum, Clostridium absonum, Clostridium pasteurianum,* and *Xanthomonas maltophilia* that produce 7α-HSDH and 7β-HSDH are used to implement the biological transformation from CDCA into UDCA. However, high-concentration CDCA inhibits the accumulation of cell biomass, making it difficult to recycle and purify products. In addition, previous researches show that as the culture time elapses, the yield of intermediates increases, and UDCA decreases, making it impossible to implement industrial production. In recent years, the joint application of 7α-HSDH and 7β-HSDH to generate UDCA with CDCA as a substrate by using a two-step method becomes a research hotspot. At present, a comprehensive transformation rate that has been researched can exceed 90%. However, a reaction amount is only at a milliliter level and is still far from industrial production. The major limitative bottlenecks are as follows:

1) A key enzyme 7β-HSDH in the two-step method with CDCA as a substrate is extremely unstable. The enzyme is active enough, but quickly becomes inactive in a catalysis reaction system.
2) The reaction system in the two-step method can carry an excessively low substrate amount (with a volume ratio of 1%), and the system is unstable.
3) Two key enzymes in the two-step method face the problem of large-scale sources in industrial application.
4) The costs of separating and purifying enzyme protein are excessively high.

SUMMARY

To resolve the foregoing problems in the prior art, the present invention provides a production method of high-purity UDCA, constructs engineered bacteria co-expressing multiple enzymes, and implements efficient production of UDCA. The present invention provides recombinant engineered bacteria that can produce UDCA at low costs. In addition, the present invention is intended to resolve the technical problems of strain construction and application.

To achieve the foregoing objectives, the following technical solutions are adopted in the present invention:

A first objective of the present invention is to provide recombinant *E. coli* that can produce UDCA at low costs. The recombinant *E. coli* may simultaneously express two enzymes, which are respectively 7β-HSDH and glucose dehydrogenase (GDH). The recombinant *E. coli* has been deposited in the China Center for Type Culture Collection on Dec. 27, 2021. The deposition number thereof is CCTCC NO: M20211644.

Preferably, the 7β-HSDH comes from *clostridium absonum,* and the GenBank login number thereof is JN191345.1.

Preferably, the GDH comes from *Bacillus subtilis,* and the GenBank login number thereof is NC-000964.

Preferably, a codon optimization is respectively performed on genes of the 7β-HSDH and the GDH, and nucleotide sequences of the genes of the 7β-HSDH and the GDH are encoded, as shown in SEQ ID NO: 1 and SEQ ID NO: 2 respectively.

Preferably, for the recombinant bacteria, the genes encoding the 7β-HSDH and the GDH are both connected to a plasmid to construct a double-gene co-expressed recombinant plasmid, and then the recombinant plasmid is transformed into a corresponding strain to obtain recombinant engineered bacteria.

Preferably, the recombinant *E. coli* is specifically constructed by using the following method:

(1) respectively performing the codon optimization on the genes of the 7β-HSDH and the GDH, and performing a complete gene synthesis;
(2) connecting the synthesized gene of the 7β-HSDH to a vector pETDuet1, to obtain a recombinant plasmid pETDuet1-7β-HSDH;
(3) transferring the pETDuet1-7β-HSDH into an *E. coli* DH5α competent cell, to obtain *E. coli* DH5α-pETDuet1-7β-HSDH carrying the recombinant plasmid;
(4) applying the *E. coli* DH5α-pETDuet1-7β-HSDH to an antibiotic solid plate, and performing screening to obtain a positive transformant (the objective of steps 3 and 4 is to perform screening by using a resistance gene carried in a plasmid to obtain a recombinant plasmid with successful connection);

(5) connecting the synthesized gene of the GDH into the vector pETDuet1-7β-HSDH, to obtain a recombinant plasmid pETDuet1-GDH-7β-HSDH;

(6) transferring the pETDuet1-GDH-7β-HSDH into an *E. coli* BL21(DE3) competent cell, to obtain *E. coli* BL21 (DE3)-pETDuet1-GDH-7β-HSDH carrying the recombinant plasmid; and (7) applying the *E. coli* BL21(DE3)-pETDuet1-GDH-7β-HSDH to an antibiotic solid plate, to perform screening to obtain a positive transformant, to obtain the recombinant *E. coli*.

Preferably, the recombinant *E. coli* is constructed with the *E. coli* BL21(DE3) as a host.

A second objective of the present invention is to provide a production method of UDCA. In the method, production is performed by using any foregoing recombinant *E. coli* of the present invention.

Preferably, the production method of UDCA is performing complete cell transformation production.

Preferably, a system of the complete cell transformation production includes cells with a wet weight of 1 g/L to 100 g/L, 7-oxo-lithocholic acid with a concentration of 1 g/L to 200 g/L, and glucose with a concentration of 1 g/L to 100 g/L; a pH is 7.0 to 9.0; and reactions occur at 1° C. to 30° C. for 1 hour to 48 hours.

Beneficial Effects

Disclosed in the present invention is a production method of high-purity UDCA. The present invention constructs novel double-enzyme co-expression gene engineered bacteria. The bacteria are applicable to the production of high-purity UDCA. The yield of a target product is increased through the joint expression and application of 7β-HSDH and GDH. The method in the present invention is simple, generates a small amount of impurities in a process, is a green process that satisfies environmental protection requirements, and has significant industrial application value.

DESCRIPTION OF THE EMBODIMENTS

Figure 1:
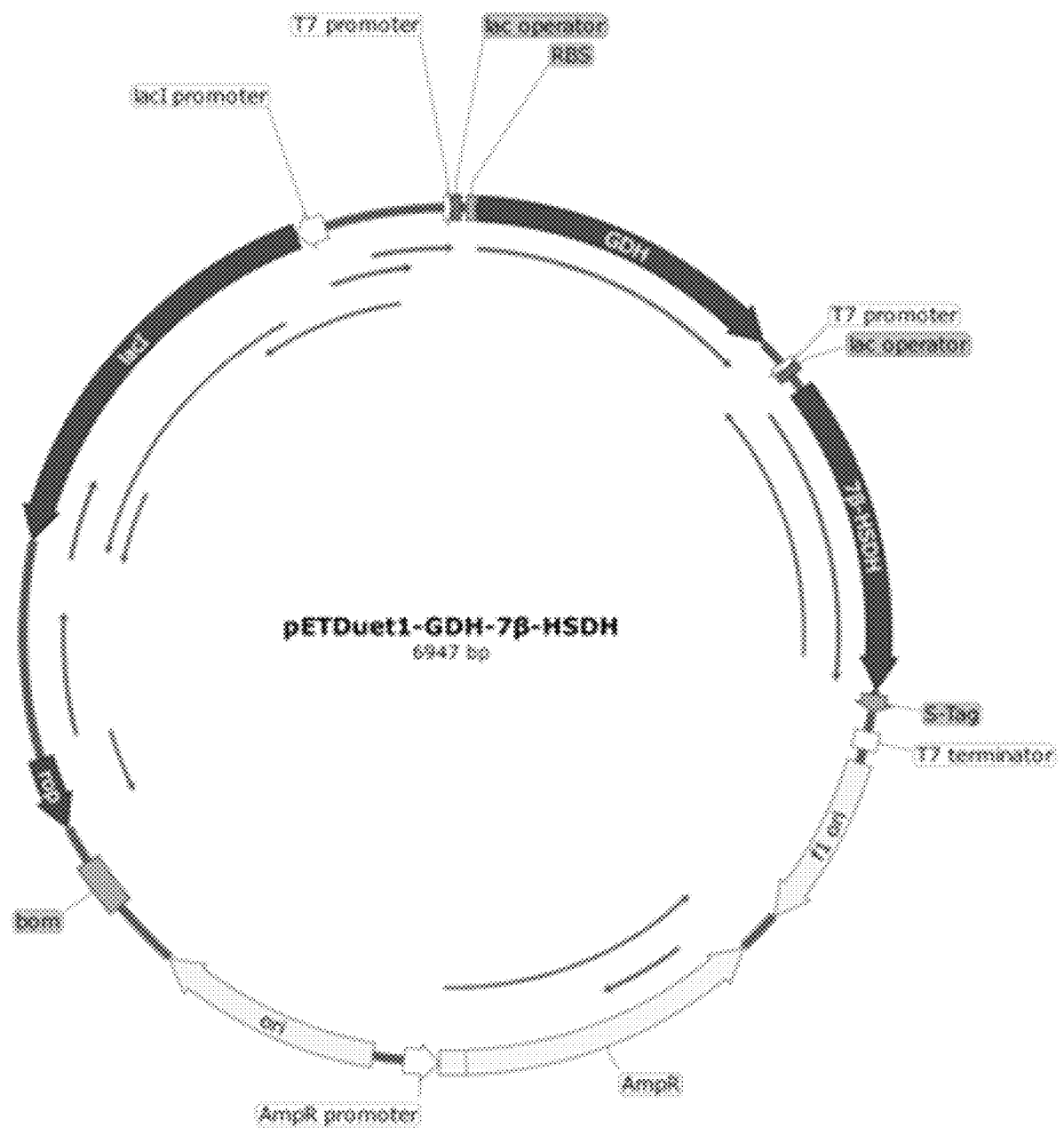
FIG. 1 is the profile of a recombinant plasmid pETDuet1-GDH-7β-HSDH.

The present invention is described below in detail. Before proceeding with the description, it is to be understood that the terms used in this specification and the appended claims are not to be construed as limited to their ordinary and dictionary meanings, but are to be interpreted in accordance with the meanings and concepts corresponding to the technical aspects of the present invention, based on the principle of allowing the inventor to define terms appropriately for the best interpretation. Therefore, the description presented herein is merely a preferred example for the purpose of description and is not intended to limit the scope of the present invention, so that it should be understood that other equivalent ways or improvements may be obtained therefrom without departing from the spirit and scope of the present invention.

The following embodiments are merely enumerated as examples of embodiments of the present invention and do not constitute any limitation to the present invention, and it is understood by those skilled in the art that modifications within the scope of not deviating from the substance and conception of the present invention fall within the scope of protection of the present invention. Unless otherwise specified, the reagents and instruments used in the following embodiments are all commercially available products.

The functional core of engineered bacteria in the present invention lies in that two enzymes, that is, 7β-HSDH and GDH, can be simultaneously expressed. The principle of engineered bacteria is that in a complete cell of the engineered bacteria, glucose is dehydrogenated by using the GDH with NADP as a coenzyme to generate gluconic acid and NADPH. The 7β-HSDH recovers 7-oxo-lithocholic acid into UDCA by using the NADPH generated in the process of dehydrogenating glucose, and at the same time the regeneration of the coenzyme NADP is implemented.

1. Strain and Plasmid Used in the Present Invention

For genes of the 7β-HSDH and the GDH, Sangon Biotech (Shanghai) Co., Ltd. performs a codon optimization and a complete gene synthesis on a gene sequence according to codon bias of *E. coli*. An *E. coli* BL21(DE3) strain is purchased from Sangon Biotech (Shanghai) Co., Ltd. The plasmid pETDuet1 is purchased from Shanghai Linyuan Biotechnology Co., Ltd.

2. *E. coli* that Co-Expresses the 7β-HSDH and the GDH is Constructed by Using the Following Method:

(1) performing the codon optimization on the genes of the 7β-HSDH and the GDH respectively, performing the complete gene synthesis, and encoding nucleotide sequences of the genes of the 7β-HSDH and the GDH, as shown in SEQ ID NO: 1 and SEQ ID NO: 2 respectively;

(2) sequentially connecting two synthesized genes to a vector pETDuet1 respectively, to obtain a recombinant plasmid pETDuet1-GDH-7β-HSDH co-expressing the 7β-HSDH and the GDH;

(3) transferring the pETDuet1-GDH-7β-HSDH into an *E. coli* BL21(DE3) competent cell, to obtain engineered bacteria BL21(DE3)-pETDuet1-GDH-7β-HSDH carrying the recombinant plasmid; and (4) culturing the engineered bacteria: inoculating the engineered bacteria into an LB liquid culture medium (10 g/L of tryptone, 5 g/L of yeast extract, and 10 g/L of sodium chloride) to perform culture, to obtain *E. coli* co-expressing the 7β-HSDH and the GDH.

3. Culture of the Engineered Bacteria Includes the Following Steps:

(1) inoculating the engineered bacteria into an LB solid plate culture medium (10 g/L of tryptone, 5 g/L of yeast extract, 10 g/L of sodium chloride, and 15.0 g/L of agar) for activation, performing activation and culture at 37° C. for 16 h to 20 h, picking a single colony from the LB solid plate culture medium, inoculating the single colony into an Erlenmeyer flask with an LB liquid culture medium containing 100 m g/L of ampicillin (Amp⁺), and performing shaking culture at 200 rpm/min and 37° C. for 16 h to 20 h;

(2) transferring the culture in step (1) into a TB liquid culture medium (12 g/L of tryptone, 24 g/L of yeast extract, 5 g/L of glycerol, 9.4 g/L of dipotassium phosphate, and 2.2 g/L of monopotassium phosphate) containing 100 m g/L of ampicillin (Amp⁺) with a ratio of 1:100, performing shaking culture at 200 rpm/min and 37° C. for 4 h to 6 h, adding 0.4 mM of isopropyl- β-D-1-thiogalactopyranoside (IPTG), and continuing with the culture at 25° C. for 10 h to 16 h, to obtain engineered bacteria of *E. coli* co-expressing the 7β-HSDH and the GDH; and (3) after induced expression ends, centrifugally collecting cells at 4° C. and 8000 rpm for 10 minutes.

4. Production of UDCA Through Complete Cell Transformation

A system of the cell transformation production includes: cells with a wet weight of 1 g/L to 100 g/L, 7-oxo-lithocholic acid with a concentration of 1 g/L to 200 g/L, and glucose with a concentration of 1 g/L to 100 g/L; a pH is 7.0 to 9.0; and reactions occur at 1° C. to 30° C. for 1 hour to 48 hours. After the transformation ends, the yield and conformation of UDCA are measured by using liquid chromatography.

5. Detection and Analysis of a Sample

The chromatographic conditions are: an RID detector is used, a mobile phase is acetonitrile (50)-water (0.0125% phosphoric acid) (50), a flow rate is 1 mL/min, a column temperature is 35° C., and a sample size is 10 μL.

To make the technical problems, technical solutions, and beneficial effects to be solved by the present invention more clearly understood, the present invention is described blow in detail in conjunction with the embodiments. It should be noted that the specific embodiments described herein are used only to explain the present invention and are not intended to limit the present invention.

Example 1

Construction of Engineered Bacteria

1. The culture of *E. coli* containing a plasmid PUC57-7β-HSDH and *E. coli* containing a vector pETDuet1 was expanded. 10 μl of the sample was taken and added to 5 mL of an LB (Amp⁺) culture medium. The culture was performed in a shaker at 37° C. for 12 h to 16 h, and the speed of the shaker was 200 rpm/min.

2. The cultured plasmid *E. coli* was extracted by using a column plasmid mini-preps kit purchased from Sangon Biotech (Shanghai) Co., Ltd. Operations were performed according to the operating instructions of the kit.

3. The plasmid PUC57-7β-HSDH and the vector pET-Duet1 were respectively extracted through double digestion with EcoRV and XhoI. A digestion system is shown in Table 1 below:

TABLE 1

| Digestion system | |
| --- | --- |
| ddH₂O | 7 μL |
| 10 × Tango buffer | 4 μL |
| EcoRV | 2 μL |
| XhoI | 2 μL |
| DNA | 5 μL |

The digestion was performed at 37° C. 3 h to 6 h. A target segment and a linear vector were recycled and purified by using a column DNA gel extraction kit purchased from Sangon Biotech (Shanghai) Co., Ltd.

4. The recycled target gene segment 7β-HSDH and the linear vector pETDuet1 were connected by using the T4 DNA ligase. The system is shown in Table 2 below:

TABLE 2

| Connection system | |
| --- | --- |
| Linear vector pETDuet1 | 4 μL |
| Inserted segment 7β-HSDH | 8 μL |
| 10 × Ligase buffer | 2 μL |
| T4 DNA Ligase | 1 μL |
| ddH₂O | 5 μL |

Connection was performed at 22° C. for 30 min to 60 min

5. The connection system transforms an *E. coli* DH5α competent cell

A 10-μL system was transferred on a super-clean bench into chemically competent *E. coli* DH5α prepared according to a standard solution. The mixture was lightly and evenly mixed and placed on ice for 30 min.

A heat shock was performed at 42° C. for 60 s. The mixture was placed on ice for 2 min. 700 μL of a sterilized LB culture medium was added on the super-clean bench.

The mixture was placed in a shaker at 37° C. and 200 rpm, was activated for 40 min to 60 min, and was applied to an LB (Amp⁺) solid plate culture medium.

The applied plate was placed in an incubator at 37° C. Inverted culture was performed for 12 h to 16 h.

6. Colony PCR detection of positive clones

Forward and reverse primers for amplifying 7β-HSDH are respectively DuetUP2 and T7t.

A PCR reaction system is shown in Table 3 below:

TABLE 3

| PCR reaction system | |
| --- | --- |
| DuetUP2 | 1 μL |
| T7t | 1 μL |
| 10 × PCR buffer | 5 μL |
| dNTP (each 10 mM) | 1 μL |
| MgCl₂ (25 mM) | 3 μL |
| Taq DNA Polymerase | 1 μL |
| ddH₂O | 38 μL |

Dominant colonies were picked on the super-clean bench by using a sterile inoculation ring, and were dipped in a PCR tube for use as a template.

PCR amplification conditions are as follows:

94° C. for 3 min; (94° C. for 30 s, 60° C. for 30 s, and 72° C. for 1 min)×32 cycles; 72° C. for 10 min; and 4° C. for storage.

7. A PCR product was detected through electrophoresis. A positive colony DH5a-pETDuet1-7β-HSDH carrying the target segment was chosen.

The foregoing positive colony was picked on the super-clean bench. 5 mL of an LB (Amp⁺) liquid culture medium was added. The mixture was shaken in a shaker at 37° C. and 200 rpm. The culture was performed for 12 h to 16 h.

8. The culture of *E. coli* containing a plasmid PUC57-GDH was expanded at the same time. 10 μL of the sample was taken. 5 mL of an LB (Amp⁺) culture medium was added. The mixture was cultured in a shaker at 37° C. for 12 h to 16 h. The speed of the shaker was 200 rpm/min.

The foregoing cultured positive bacteria plasmid and plasmid PUC57-GDH were extracted by using a column plasmid mini-preps kit from Sangon Biotech (Shanghai) Co., Ltd., and the plasmid PUC57-GDH and a vector pETDuet1-7β-HSDH were extracted by using through double digestion with EcoRI and HindIII. The digestion system was the same as that in the foregoing 3. Gel recycling was performed on the target gene segment and the linear vector.

9. The recycled GDH target gene and the linear vector pETDuet1-7β-HSDH were connected. A connection system was the same as that in the foregoing 4.

10. The connection system was transformed into *E. coli* DH5α competent cells. The operation was the same as that in the foregoing 5.

11. Colony PCR detection of positive clones: The GDH was amplified by using forward and reverse primers pET Upstream and DuetDOWN1. A PCR product was detected through electrophoresis. The positive colony pETDuet1-GDH-7β-HSDH carrying the target segment was obtained through screening. The conditions of the PCR reaction system and the cycles were the same as those in the foregoing 6.

12. Positive clone bacteria were picked. 5 mL of an LB (Amp⁺) liquid culture medium was added. The mixture was shaken in a shaker at 37° C. and 200 rpm. The culture was performed for 12 h to 16 h. A plasmid was extracted. Digestion and verification were performed to determine that a vector was correctly constructed. The profile of the vector is shown in FIG. 1.

13. The recombinant plasmid was transferred to an *E. coli* BL21(DE3) expression strain, to obtain engineered bacteria BL21(DE3)-pETDuet1-GDH-7β-HSDH.

14. Culture of engineered bacteria

The engineered bacteria were inoculated into an LB solid plate culture medium for activation. Activation and culture were performed at 37° C. for 16 h to 20 h. A single colony was picked from the LB solid plate culture medium and was inoculated into an Erlenmeyer flask with an LB liquid culture medium containing 100 m g/L of ampicillin (Amp⁺), and shaking culture was performed at 200 rpm/min and 37° C. for 16 h to 20 h.

The foregoing culture was transferred into a TB liquid culture medium containing 100 m g/L of ampicillin (Amp⁺) with a ratio of 1:100. Shaking culture was performed at 200 rpm/min and 37° C. for 4 h to 6 h. 0.4 mM of IPTG was added. Culture was continued at 25° C. for 10 h to 16 h. A resultant was saved as the engineered bacteria for future use.

The LB solid culture medium includes the following components: 10 g/L of tryptone, 5 g/L of yeast extract, 10 g/L of sodium chloride (NaCl), and 15.0 g/L of agar.

The LB liquid culture medium includes the following components: 10 g/L of tryptone, 5 g/L of yeast extract, and 10 g/L of sodium chloride (NaCl).

The TB liquid culture medium includes the following components: 12 g/L of tryptone, 24 g/L of yeast extract, 5 g/L of glycerol, 9.4 g/L of dipotassium phosphate ($K_2HPO_4$), and 2.2 g/L of monopotassium phosphate ($KH_2PO_4$).

Example 2

According to an induced expression method in Example 1, after induced expression is completed, the bacteria body was collected. In a 100-mL reaction system, the wet weight of cells was 3 g/L, glucose was 4 g/L, 7-oxo-lithocholic acid was 7 g/L, the pH=8.0, and the temperature was 10° C. The transformation was performed for 10 h, during which 1M NaOH was used to control the pH at 8.0±0.2.

Figure 2:
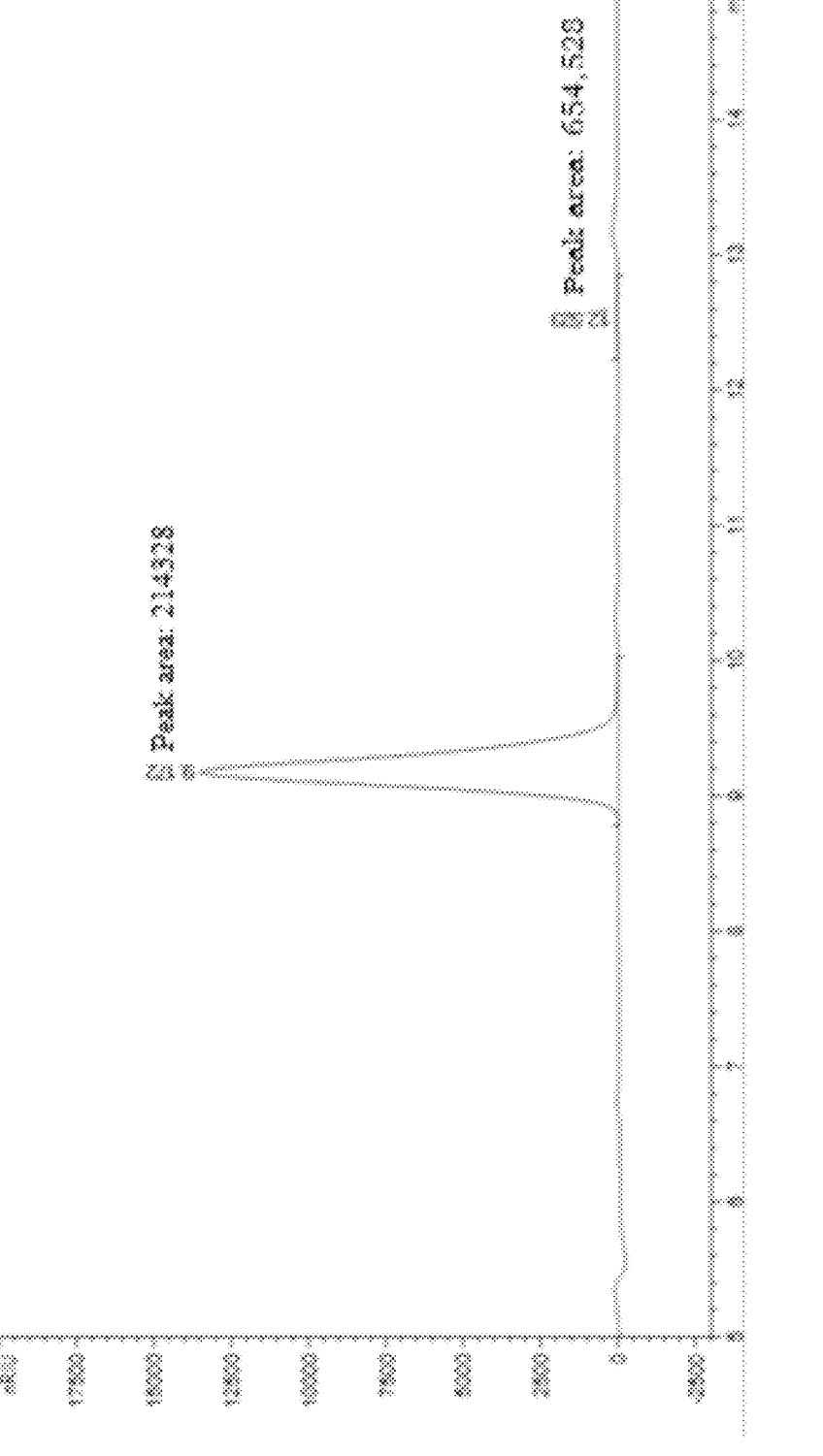
FIG. 2 is the profile of a liquid phase detection result of the reaction of generating UDCA using 7-oxo-lithocholic acid under the catalysis of engineered bacteria for UDCA.

FIG. 2 is the profile of a liquid phase detection result of the reaction of generating UDCA using 7-oxo-lithocholic acid under the catalysis of engineered bacteria for UDCA. 7-oxo-lithocholic acid with the liquid chromatography detection >99% was transformed to generate UDCA.

The transformation and construction of the foregoing enzymes and gene engineered bacteria co-expressing the enzymes, the culture medium components and culture method of the bacteria body, and the complete cell biological transformation are only preferred examples of the present invention, and are not used to limit the present invention. Theoretically, other bacteria, filamentous fungi, actinomycetes, and zooblasts may all undergo genome transformation and are used for complete cell catalysis of multiple-gene co-expression. Any modification and equivalent replacement may be made within the principle and spirit of the present invention.

---

What is claimed is:

1. A recombinant *Escherichia coli* (*E. coli*), wherein the recombinant *E. coli* simultaneously expresses 7β-hydroxysteroid dehydrogenase (7β-HSDH) and glucose dehydrogenase (GDH), wherein the recombinant *E. coli* is constructed by using following steps:

(1) performing a codon optimization on genes of the 7β-HSDH and the GDH, and performing a complete gene synthesis, respectively;

(2) first connecting the synthesized gene of the 7β-HSDH to a vector pETDuet1, to obtain a recombinant plasmid pETDuet1-7β-HSDH, and then connecting the gene of the GDH to the plasmid pETDuet1-7β-HSDH, to obtain a recombinant plasmid pETDuet1-GDH-7β-HSDH co-expressing the 7β-HSDH and the GDH;

(3) transferring the pETDuet1-GDH-7β-HSDH into an *E. coli* BL21(DE3) competent cell, to obtain *E. coli* BL21 (DE3)-pETDuet1-GDH-7β-HSDH carrying the recombinant plasmid; and (4) culturing the *E. coli* BL21(DE3)-pETDuet1-GDH-7β-HSDH, to obtain the recombinant *E. coli*;

wherein in step (1), after the codon optimization, the 7β-HSDH comprises a sequence of SEQ ID NO:1 and the GDH comprises a sequence of SEQ ID NO: 2;

wherein in step (4), the culture of *E. coli* comprises the following steps:

inoculating the *E. coli* BL21(DE3)-pETDuet1-GDH-7β-HSDH into a lysogeny broth (LB) solid plate culture medium for activation and culture, then picking a single colony from the LB solid plate culture medium, inoculating the single colony into an Erlenmeyer flask with an LB liquid culture medium containing 100 mg/L of ampicillin (Amp⁺), and performing shaking culture;

transferring the culture from inoculating the *E. coli* BL21 (DE3)-pETDuet1-GDH-7β-HSDH into a tuberculosis (TB) liquid culture medium containing 100 mg/L of ampicillin (Amp⁺), performing shaking culture for a period of time, then adding 0.4 mM of isopropyl-β-D-1-thiogalactopyranoside (IPTG), and continuing with the culture; and after induced expression ends, centrifugally collecting cells, to obtain the recombinant *E. coli* as engineered bacteria;

wherein the LB solid plate culture medium comprises the following components: 10 g/L of tryptone, 5 g/L of yeast extract, 10 g/L of sodium chloride, and 15.0 g/L of agar; the LB liquid culture medium comprises the following components: 10 g/L of tryptone, 5 g/L of yeast extract, and 10 g/L of sodium chloride; and the TB liquid culture medium comprises the following components: 12 g/L of tryptone, 24 g/L of yeast extract, 5 g/L of glycerol, 9.4 g/L of dipotassium phosphate, and 2.2 g/L of monopotassium phosphate; and wherein the recombinant *E. coli* is adapted for producing ursodeoxycholic acid (UDCA) using 7-oxo-lithocholic acid with a conversion rate of greater than 99%.

*     *     *     *     *

SEQUENCE LISTING

```
Sequence total quantity: 2
SEQ ID NO: 1          moltype = DNA   length = 786
FEATURE               Location/Qualifiers
misc_feature          1..785
                      note = 7Beta-HSDH
source                1..786
                      mol_type = other DNA
                      organism = Clostridium absonum
SEQUENCE: 1
atgaatttta gagaaaaata tggacaatgg ggaattgttt taggggcaac agaaggaatt   60
ggtaaagcta gtgcttttga attagctaaa agagggatgg atgttatttt agttggaaga  120
agaaaagaag cattagaaga gttagctaag gcaatacatg aagaaacagg aaaagaaatc  180
agagtattac cacaagattt atctgaatat gatgctgcag aaagattaat agaagcaact  240
aaagatttag atatgggagt cattgagtat gttgcatgtc tacatgcaat gggacaatat  300
aataaagttg actacgctaa atatgaacaa atgtatagag ttaatataag aacattctca  360
aaattattac atcactatat aggtgaattc aaagaaagag atagaggtgc attcataaca  420
ataggatctt tatcaggatg gacatcatta ccattctgtg cagaatatgc agcagaaaaa  480
gcttatatga tgacagtaac agaaggagtt gcttacgaat gtgcaaatac taatgttgac  540
gtaatgcttt tatcagcggg ttcaacaatc acacctactt ggttaaaaaa taaaccatca  600
gatcctaagg cggttgcagc agcaatgtat ccagaagatg ttataaaaga tggatttgaa  660
caattaggaa agaaatttac ttatttagct ggagagttaa atagagaaaa aatgaaggaa  720
aataatgcaa tggatagaaa tgatttaatt gcaaaactag gaaaaatgtt tgatcatatg  780
gcataa                                                             786

SEQ ID NO: 2          moltype = DNA   length = 786
FEATURE               Location/Qualifiers
misc_feature          1..786
                      note = GDH
```

-continued

```
source               1..786
                     mol_type = other DNA
                     organism = Bacillus subtilis
SEQUENCE: 2
atgtatacag atttaaaaga taaagtagta gttgtaacag gcggatcaaa aggattgggt    60
cgcgcaatgg ccgttcgttt tggtcaagag cagtcaaaag tggttgtaaa ctaccgcagc   120
aatgaagaag aagcgctaga agtaaaaaaa gaaattgaac aagctggcgg ccaagcaatt   180
attgttcgag gcgacgtaac aaaagaggaa gacgttgtga atcttgtaga gacagctgtt   240
aaagagtttg gcacattaga cgttatgatt aacaatgctg gtgttgaaaa cccggttcct   300
tcacatgaat tatcgttaga aaactggaat caagtaatcg atacaaactt aacaggcgcg   360
tttttaggaa gccgcgaagc gattaaatat tttgttgaaa atgatattaa aggaaacgtt   420
attaacatgt ccagcgttca cgagatgatt ccttggccac tatttgttca ctatgcagca   480
agtaaaggcg gtatgaaact aatgacagaa acattggctc ttgaatatgc gccaaaaggt   540
atccgcgtaa ataacattgg accaggcgcg atcgatacgc caatcaacgc tgaaaaattc   600
gcagatccgg aacagcgtgc agacgtagaa agcatgattc caatgggcta catcggcaac   660
ccggaagaaa ttgcatcagt tgcagcattc ttagcatcgt cacaagcaag ctacgtaaca   720
ggtattacac tatttgctga tggcggtatg acaaaatatc cttctttcca agcgggaaga   780
ggttaa                                                              786
```